United States Patent [19]
Shiraishi et al.

[11] Patent Number: 5,733,344
[45] Date of Patent: Mar. 31, 1998

[54] TEMPORARY HAIR DYES CONTAINING A DISPERSANT, TITANIUM BLACK, PIGMENTS AND AN ALCOHOLIC SOLVENT, AND PROCESSES OF PRODUCING TEMPORARY HAIR DYES

[75] Inventors: Katsuhiko Shiraishi, Fujioka; Kiyokazu Sakurai, Saitama; Tetsuo Kosaka, Gunma; Tomoko Hasegawa, Maebashi; Kazuhiro Ami, Fujioka; Takashi Umeno, Gunma, all of Japan

[73] Assignee: Mitsubishi Pencil Kabushiki Kaisha, Tokyo, Japan

[21] Appl. No.: 758,009

[22] Filed: Nov. 27, 1996

[30] Foreign Application Priority Data

Nov. 30, 1995 [JP] Japan ................... 7-334269

[51] Int. Cl.⁶ ............................................ A61K 7/13
[52] U.S. Cl. ...................... 8/435; 8/405; 8/554; 8/637.1
[58] Field of Search ....................... 8/405, 435, 554, 8/637.1

[56] References Cited

U.S. PATENT DOCUMENTS

| 5,403,357 | 4/1995 | Tsujino ............................ 8/435 |
| 5,597,386 | 1/1997 | Igarashi et al. ............................ 8/405 |

FOREIGN PATENT DOCUMENTS

| 716845 | 6/1996 | European Pat. Off. . |
| 62-198608 | 9/1987 | Japan . |
| 3-63212 | 3/1991 | Japan . |
| 6-336411 | 12/1994 | Japan . |

*Primary Examiner*—Paul Lieberman
*Assistant Examiner*—Caroline L. Dusheck
*Attorney, Agent, or Firm*—Darby & Darby

[57] ABSTRACT

The present invention provides a temporary hairdye which is excellent in dispersion stability of a pigment even after storage over a long period of time by dispersing titanium black, which is safe to a human body, in alcohol having 4 or less carbon atoms, primarily ethanol by using an N-methacryloylethyl-N,N-dimethylammonium.α-N-methylcarboxybetain.butyl methacrylate copolymer. Further, there can be prepared a temporary hairdye which increases dispersion stability of the pigments and provides a different hue by subjecting titanium black and other pigments, particularly iron oxide type pigments such as iron oxide red, black iron oxide and yellow iron oxide to dispersion treatment together.

6 Claims, 1 Drawing Sheet

TEMPORARY HAIR DYES CONTAINING A DISPERSANT, TITANIUM BLACK, PIGMENTS AND AN ALCOHOLIC SOLVENT, AND PROCESSES OF PRODUCING TEMPORARY HAIR DYES

BACKGROUND OF THE INVENTION (1) Field of the Invention

A hairdye for dyeing primarily hair includes oxidation hairdyes which develop a color in hairs to be colored, acid hairdyes which cause dyes to be adsorbed on hairs to be colored and temporary hairdyes which form colored films on hairs to be colored. The present invention relates to a temporary hairdye, particularly to a hairdye which does not use carbon black and graphite.

(2) Description of the Related Art

Conventional temporary hairdyes include hairdyes in which carbon black is dispersed in water or ethanol and a resin is used in combination to form a colored film of a so-called dark color such as black and brown on hairs to conceal primarily white hairs, and hairdyes in which color pigments such as titanium white and tar pigments are used in combination to cover colors of hairs to color them optionally.

Carbon black is used primarily for covering white hairs because it has the advantages that carbon black has a high coloring power and an excellent covering property and that since carbon black can readily be dispersed and has a small specific gravity, it is less liable to settle down even after storage over a long period of time and is inexpensive.

It has been allowed to use carbon black for cosmetic in Japan, but it is never allowed in U.S. to use carbon black for cosmetics because of possibility of carcinogenesis. Accordingly, a temporary hairdye using no carbon black has been desired.

Titanium white, that is, titanium oxide is a pigment having such a high covering power as covering even black color of hairs, and the covering power of titanium white increases the colors of pigments other than titanium white.

However, titanium oxide is white and can not dye white hairs to dark colors.

It is expected from these facts that a dark color temporary hairdye using no carbon black can be obtained by using dark color titanium oxide, for example, titanium black. However, titanium oxide has a large specific gravity as compared with that of carbon black and is markedly inferior in stability in dispersion. A coloring power of titanium black is strong as compared with those of other pigments but weaker than that of carbon black, and therefore titanium black is required in 3 to 4 times as large amount as carbon black in terms of weight in order to obtain almost the same coloring power on white hairs.

A resin is used for dispersing a pigment. However, conventional dispersing resins have had the defects that when the amount of a dispersing resin is small, pigment particles contained in a coating on a hair has a weak binding power and is liable to fall down by rubbing and therefore a lot of the dispersing resin is required in order to obtain a sufficient binding power, which results in increasing a thickness of a coating on a hair and growing a stiff feeling.

SUMMARY OF THE INVENTION

An object of the present invention is to provide a temporary hairdye which is safe to a human body, good in feeling and has a good dispersibility of a pigment and an excellent fixing property and which has a notably slow precipitation rate or can readily be redispersed by shaking.

Intensive researches made by the present inventors in order to solve the problems described above have resulted in successfully obtaining a dispersion which is stable against precipitation and coagulation by using an N-methacryloylethyl-N,N-dimethylammonium.α-N-methylcarboxybetain.butyl methacrylate copolymer to disperse titanium black, that is, a titanium.titanium oxide sintered substance (name of titanium black in "Ingredient Specification out of Cosmetic Material Standard") in an alcoholic solvent, primarily ethanol. Further, it has been found that dispersing titanium black together with iron oxide type pigments such as iron oxide red provides the effect to control as well coagulation and precipitation of the iron oxide type pigments, and thus the present invention has been completed.

Figure 1:
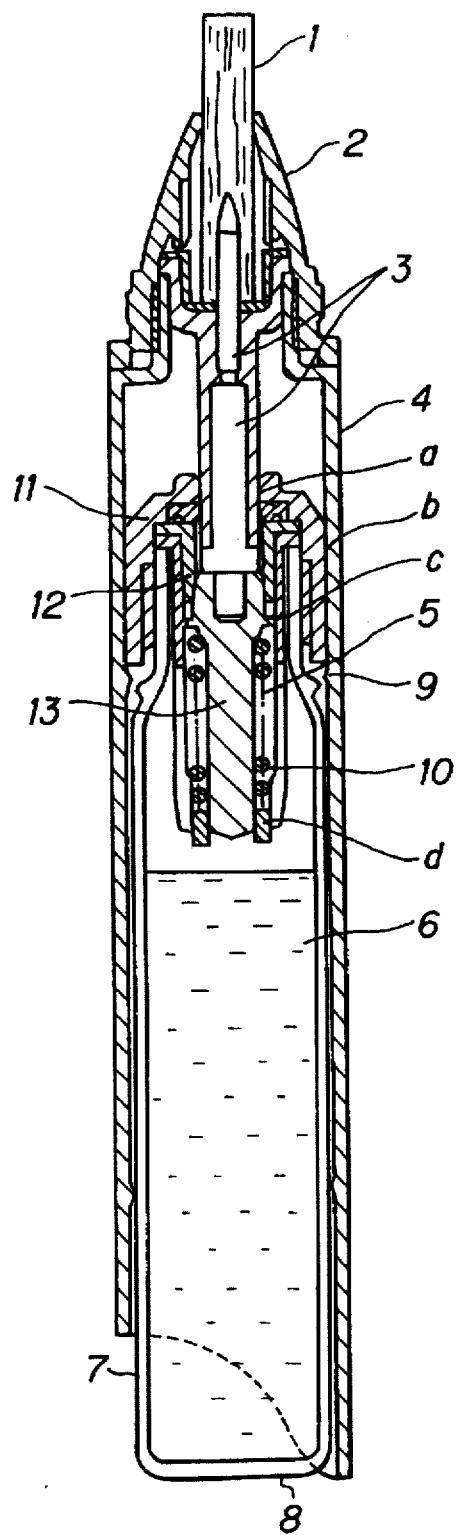
FIG. 1 is a cross section of an applicator filled with a hairdye prepared in the examples of the present invention and the comparative examples. The symbols of the figure represent.

1 Applying part (brush)
2 Mouthpiece (made of plastic)
3 Liquid introducing part
4 Barrel cylinder
5 Valve
6 Coating liquid
7 Coating liquid storage tube (inner barrel)
8 Knock part
9 Stopper
10 Spring in valve
11 Cap for coating liquid storage tube
12 Valve seat
13 Valve rod
  a sliding face
  b sliding face
  c sliding face
  d sliding face

DETAILED DESCRIPTION OF THE PREFERRED EMBODIMENTS

In this temporary hairdye, it is essential to disperse titanium black by using the N-methacryloylethyl-N,N-dimethylammonium.α-N-methylcarboxybetain.butyl methacrylate copolymer, and the above temporary hairdye is characterized in using no carbon black.

Titanium black alone can color white hairs, but arranging color to brown color through reddish or yellowish black color by using titanium black in combination with iron oxide red, yellow iron oxide or black iron oxide gives more natural color to hairs.

The N-methacryloylethyl-N,N-dimethylammonium.α-N-methylcarboxybetain.butyl methacrylate copolymer exhibits an effect as a dispersant usually in an amount of 0.1% or more based on the whole hairdye, though depending on required amounts of titanium black and other dispersed pigments and kinds thereof. The amount less than the above range can not provide a stable dispersing effect or can not disperse a required amount of pigments.

In the case where the N-methacryloylethyl-N,N-dimethylammonium.α-N-methylcarboxybetain.butyl methacrylate copolymer is added in a large quantity, while waterproof, strength against falling down caused by rubbing, and stability against precipitation of a pigment are excellent, caused are the disadvantages that an aging stability of a coating liquid is a little inferior and that a coated film is thickened too much and provides hairs with stiffness and the viscosity is so increased as to deteriorate a coating property. Accordingly, the maximum addition amount is about 20%.

An addition amount of the N-methacryloylethyl-N,N-dimethylammonium.α-N-methylcarboxybetain.butyl methacrylate copolymer falls preferably in a range of 0.3 to 10% in terms of practical use.

This is because of the following reasons. That is, a blend amount of a pigment such as titanium black used for coloring white hairs to such an extent that coloring is not conspicuous and for obtaining natural hue and feeling is about 1~10%, and a minimum blend amount of the resin required for dispersing stably about 1% of the pigment is 0.3%, and the maximum addition amount in which a natural feeling to be important in concealing white hairs is not lost is 10%. When the resin is blended in a large amount in order to improve durability of the coated film for coping with falling caused by rubbing, caused is the disadvantage that hairs become stiff or have unnatural gloss. It falls more preferably in a range of 2 to 8%. The waterproof, strength against rubbing and natural feeling are best balanced in this range.

Alcohols having 4 or less carbon atoms are preferred as the principal solvent for the temporary hairdye of the present invention. In particular, ethanol is preferred. However, any solvent can be used as long as it is safe to a human body and can dissolve the N-methacryloylethyl-N,N-dimethylammonium.α-N-methylcarboxybetain.butyl methacrylate copolymer. The solvents having higher volatility than that of water are advantageous because drying is fast.

Water can be the safest principal solvent, and therefore it is meaningless to use a solvent having lower volatility than that of water in view of safety.

Titanium black is used as an essential component for a coloring component, and there can be used, if necessary, inorganic pigments such as zinc oxide, iron oxide red, chromium oxide, black iron oxide, cobalt blue, alumina white, yellow iron oxide, viridian, zinc sulfide, lithopone, cadmium yellow, vermilion, cadmium red, chrome yellow, molybdate orange, zinc chromate, strontium chromate, white carbon, ultramarine blue, lead white, Prussian blue, manganese violet, aluminum powder and brass powder, organic pigments and lake pigments of acid dyes, such as C.I. 16185, C.I. 45430, C.I. 16255, C.I. 45410, C.I. 45440, C.I. 45100, C.I. 19140, C.I. 15985, C.I. 42053, C.I. 42090, C.I. 73015, C.I. 15850, C.I. 15585, C.I. 15630, C.I. 45170, C.I. 15800, C.I. 15880, C.I. 12120, C.I. 45380, C.I. 26100, C.I. 73360, C.I. 17200, C.I. 12085, C.I. 45370, C.I. 12075, C.I. 21110, C.I. 15510, C.I. 45425, C.I. 45350, C.I. 47005, C.I. 47000, C.I. 21090, C.I. 61570, C.I. 61565, C.I. 59040, C.I. 42095, C.I. 73000, C.I. 42052, C.I. 69825, C.I. 42090, C.I. 20170, C.I. 60725, C.I. 45190, C.I. 15865, C.I. 26105, C.I. 16155, C.I. 16150, C.I. 14700, C.I. 12140, C.I. 15620, C.I. 11725, C.I. 14600, C.I. 12100, C.I. 11680, C.I. 18950, C.I. 10316, C.I. 11380, C.I. 11390, C.I. 13065, C.I. 18820, C.I. 10020, C.I. 42085, C.I. 61520, C.I. 74160, C.I. 60730 and C.I. 20470, and pearl pigments such as scale foil, various mica titans, sericite, muscovite, pearl oyster shell powder, abalone shell powder, and button shell powder.

As used for cosmetics, these coloring components have to be sufficiently concerned about safety to a human body. The coloring components are selected from substances permitted for cosmetics, specifically substances permitted for food additives and substances having low oral toxicity.

Black iron oxide, iron oxide red, and yellow iron oxide not only have an excellent safety but also increases in stability against precipitation and coagulation by dispersing them together with titanium black, and therefore they are the most preferable materials.

Resins, surfactants, perfumes, oil & fats, scarcely volatile hydrocarbons, silicone oils, and water can be added, if necessary, to the temporary hairdye of the present invention.

The N-methacryloylethyl-N,N-dimethylammonium.α-N-methylcarboxybetain.butyl methacrylate copolymer is an excellent resin having the best dispersion stability for a pigment and good durability and feeling on a hair. Various factors such as a fixing property, strength against rubbing and waterproof are involved in the durability, and resins which are not good in a dispersion stability for a pigment but are sufficient for bettering any of the factor and feeling are available and used according to necessity. Surfactants exhibit the preferred effects that wetting between the temporary hairdye and a hair is raised and coating is facilitated and that waterproof is improved in interfaces between a coating, gas and liquid (sweat). Perfumes have the effects to mask odors of ethanol, the N-methacryloylethyl-N,N-dimethylammonium.α-N-methylcarboxybetain.butyl methacrylate copolymer and pigments, and raise feeling of use.

Some of scarcely volatile surfactants and perfumes, oil & fats, scarcely volatile hydrocarbons, and silicone oils are useful substances as a plasticizer for the N-methacryloylethyl-N,N-dimethylammonium.α-N-methylcarboxybetain.butyl methacrylate copolymer. Their suitable effects are to control fragility of a coating on a hair and to provide the coating which is soft and has good feeling and which has a high fixing property and excellent durability due to increased adhesion to hairs. Water is a poor solvent for the N-methacryloylethyl-N,N-dimethylammonium.α-N-methylcarboxybetain.butyl methacrylate copolymer but has the effect to fit the temporary hairdye to a hair to improve the feeling and thus provides preferred results by suitable addition thereof. In this case, the suitable amount is 20% or less, preferably 3 to 12% based on the whole amount.

One aspect of the present invention is characterized in that iron oxide red, black iron oxide, yellow iron oxide (hereinafter referred to as iron oxide type pigments) and titanium black are subjected to dispersion treatment at the same time.

Dispersibility, though expressed in a word, includes a performance to suppress precipitation itself of a pigment to maintain a homogeneous suspension system and a performance that a pigment is precipitated but redispersed by simple operations such as shaking. In the case of pigments having a high true specific gravity such as inorganic pigments, particularly titanium oxide type pigments such as titanium white and titanium black, and iron oxide type pigments, it is impossible to completely prevent precipitation, and therefore "good dispersibility" means that a precipitation rate is slow and a precipitate can easily be redispersed. The N-methacryloylethyl-N,N-dimethylammonium.α-N-methylcarboxybetain.butyl methacrylate copolymer is an excellent dispersant and well disperses the iron oxide type pigments. However, the iron oxide type pigments are easily coagulated and precipitated and tend to readily form a hard deposit (hereinafter referred to as a hard cake) which is difficult to be redispersed once precipitated.

However, subjecting titanium black and an iron oxide type pigment to dispersion treatment at the same time in the presence of the N-methacryloylethyl-N,N-dimethylammonium.α-N-methylcarboxybetain.butyl methacrylate copolymer makes it difficult to form this hard cake and improves very much redispersibility of a precipitate.

It is not certain what principle the fact is based on, but it is supposed that titanium black particles and iron oxide type pigment particles on which shearing is exerted by dispersion associate at a stage of secondary or tertiary coagulation to form an aggregate of titanium black and the iron oxide type pigment, which is then stabilized.

Accordingly, also in the case where a dispersion of titanium black prepared in advance and a dispersion of an iron oxide type pigment are put together, preferred results can be obtained by dispersing them again by means of a dispersing device such as a ball mill, a beads mill, a sand mill, a roll mill, a kneader, a homogenizer and a supersonic dispersing device.

Titanium black can also be used as a dispersion stabilizer for the iron oxide type pigments. That is, also when a small amount of titanium black is dispersed in the iron oxide type pigment, exhibited is the effect to prevent a hard cake of the iron oxide type pigment from being formed.

With respect to a quantitative standard, a sufficient effect can be obtained by adding 10% or more by weight of titanium black relative to iron oxide red. A hard cake is not observed to be formed as long as titanium black is added in an amount exceeding the above ratio. The same applies to yellow iron oxide.

In the case of black iron oxide, a hard cake of black iron oxide itself is soft as compared with those of iron oxide red and yellow iron oxide, and therefore a less amount of titanium black provides the effect.

This property is effective for industrially producing the temporary hairdye. For example, as a method of controlling scattering in hue, if four colors of dispersions of a single dispersion of titanium black, a mixed dispersion of iron oxide red and titanium black, a mixed dispersion of black iron oxide and titanium black and a mixed dispersion of yellow iron oxide and titanium black are prepared in advance, a brown color can be prepared by simple work such as stirring by means of blades without using again a dispersing device after mixing colors.

The temporary hairdye of the present invention is prepared basically by dissolving the N-methacryloylethyl-N,N-dimethylammonium.α-N-methylcarboxybetain.butyl methacrylate copolymer in ethanol, then adding pigments such as titanium black, carrying out dispersion treatment by means of a ball mill, a beads mill, a sand mill, a roll mill, a kneader, a homogenizer and a supersonic dispersing device to prepare a pigment dispersion, and further adding, if necessary, a resin, a surfactant, perfume, and pigments and a dispersion thereof in view of performances of the temporary hairdye such as durability and feeling after applying. However, no problems shall be caused if all materials are mixed at one time to carry out dispersion treatment.

EXAMPLES

Next, the present invention shall be explained in further details with reference to examples.

In the examples and comparative examples, the N-methacryloylethyl-N,N-dimethylammonium.α-N-methylcarboxybetain.butyl methacrylate copolymer is supplied under the trade name of "Yuka Former AM75" and is a 30% or 40% ethanol solution.

Example 1

| | |
|---|---|
| Tilack D (titanium black; trade name of Akoh Kasei Co., Ltd.) | 5.0 parts by weight |
| Bengara 211 (iron oxide red; trade name of Daito Kasei Co., Ltd.) | 1.0 part by weight |
| Yuka Former AM75 202 (30% ethanol solution; trade name of Mitsubishi Chemical Co., Ltd.) | 15.0 parts by weight |
| KF-56 (polyether-modified silicone; trade name of Shinetsu Chemical Co., Ltd.) | 0.5 part by weight |
| Ethanol | 78.5 parts by weight |

The above components were stirred for one hour by means of a beads mill to obtain hairdye 1.

Example 2

| [Liquid A] | |
|---|---|
| Titanium black 10S (trade name of Mitsubishi Material Co., Ltd.) | 4.0 parts by weight |
| Yuka Former AM75 201 (40% ethanol solution; trade name of Mitsubishi Chemical Co., Ltd.) | 10.0 parts by weight |
| Ethanol | 50.0 parts by weight |

The above components were stirred for one hour by means of a beads mill to obtain liquid A.

| [Liquid B] | |
|---|---|
| TODA Yellow 48 (yellow iron oxide; trade name of Toda Ind. Co., Ltd.) | 2.0 parts by weight |
| Yuka Former AM75 201 | 5.0 parts by weight |
| Ethanol | 23.0 parts by weight |

The above components were stirred for one hour by means of a beads mill to obtain liquid B.

| [Liquid C] | |
|---|---|
| Water | 5.0 parts by weight |
| Luviscol K15 (polyvinylpyrrolidone; trade name of BASF Co., Ltd.) | 1.0 part by weight |

The above components were stirred for one hour by means of a magnetic stirrer to obtain liquid C.

| | |
|---|---|
| [Liquid A] | 64.0 parts by weight |
| [Liquid B] | 30.0 parts by weight |
| [Liquid C] | 6.0 parts by weight |

The above liquids were mixed and irradiated with a supersonic wave for one hour to obtain hairdye 2.

Example 3

| | |
|---|---|
| Titanium black 20M (trade name of Mitsubishi Material Co., Ltd.) | 5.0 parts by weight |
| Red No. 202 (manufactured by Kishi Kasei Co., Ltd.) | 0.5 part by weight |
| Yuka Former AM75 R205S (30% ethanol solution; trade name of Mitsubishi Chemical Co., Ltd.) | 10.0 parts by weight |
| Ethanol | 84.5 parts by weight |

The above components were stirred for one hour by means of a sand mill to obtain hairdye 3.

Example 4

| | |
|---|---|
| Tetsuguro BL-100 (black iron oxide: trade name of Daito Kasei Co., Ltd.) | 4.5 parts by weight |
| Tilack D | 0.5 part by weight |
| Yuka Former AM75 204 (40% ethanol solution; trade name of Mitsubishi Chemical Co., Ltd.) | 12.5 parts by weight |
| Ethanol | 82.5 parts by weight |

The above components were stirred for one hour by means of a beads mill to obtain hairdye 4.

Example 5

| [Liquid D] | |
|---|---|
| Tilack D | 4.5 parts by weight |
| Yuka Former AM75 202 | 7.5 parts by weight |
| KF-56 | 0.25 part by weight |
| Ethanol | 39.25 parts by weight |

The above components were stirred for one hour by means of a beads mill to obtain liquid D.

| [Liquid E] | |
|---|---|
| Tilack D | 0.5 part by weight |
| Bengara 211 | 1.0 part by weight |
| Yuka Former AM75 202 | 7.5 parts by weight |
| KF-56 | 0.25 part by weight |
| Ethanol | 39.25 parts by weight |

The above components were stirred for one hour by means of a beads mill to obtain liquid E.

| | |
|---|---|
| [Liquid D] | 51.5 parts by weight |
| [Liquid E] | 48.5 parts by weight |

The above liquids were stirred by means of a magnetic stirrer to obtain hairdye 5.

Comparative Example 1

| | |
|---|---|
| Tilack D | 5.0 parts by weight |
| Bengara 211 | 1.0 part by weight |
| PVP K-15 (polyvinylpyrrolidone manufactured by GAF Co., Ltd.) | 4.5 parts by weight |
| KF-56 | 0.5 part by weight |
| Ethanol | 89.0 parts by weight |

The above components were stirred for one hour by means of a beads mill to obtain hairdye A.

Comparative Example 2

| [Liquid F] | |
|---|---|
| Titanium black 10S | 4.0 parts by weight |
| Julimer AT-960P (ethylene acryl resin; trade name of Nippon Junyaku Co., Ltd.) | 4.0 parts by weight |
| Ethanol | 56.0 parts by weight |

The above components were stirred for one hour by means of a beads mill to obtain liquid F.

| [Liquid G] | |
|---|---|
| TODA Yellow 48 | 2.0 parts by weight |
| Julimer AT-960P | 2.0 parts by weight |
| Ethanol | 26.0 parts by weight |

The above components were stirred for one hour by means of a beads mill to obtain liquid G.

| [Liquid C] | |
|---|---|
| Water | 5.0 parts by weight |
| Luviscol K15 | 1.0 part by weight |

The above components were stirred for one hour by means of a magnetic stirrer to obtain liquid C.

| | |
|---|---|
| [Liquid F] | 64.0 parts by weight |
| [Liquid G] | 30.0 parts by weight |
| [Liquid C] | 6.0 parts by weight |

The above liquids were mixed and irradiated with a supersonic wave for one hour to obtain hairdye B.

Comparative Example 3

| | |
|---|---|
| Bengara 211 | 3.0 parts by weight |
| Konjo 302 (Prussian blue; trade name of Daito Kasei Co., Ltd.) | 2.0 parts by weight |
| Red No. 202 | 0.5 part by weight |
| Yuka Former AM75 R205S | 10.0 parts by weight |
| Ethanol | 84.5 parts by weight |

The above components were stirred for one hour by means of a sand mill to obtain hairdye C.

Comparative Example 4

| | |
|---|---|
| Tetsuguro BL-100 | 5.0 parts by weight |
| Yuka Former AM75 204 | 12.5 parts by weight |
| Ethanol | 82.5 parts by weight |

The above components were stirred for one hour by means of a beads mill to obtain hairdye D.

Comparative Example 5

| [Liquid H] | |
|---|---|
| Tilack D | 5.0 parts by weight |
| Yuka Former AM75 202 | 7.5 parts by weight |
| KF-56 | 0.25 part by weight |
| Ethanol | 39.25 parts by weight |

The above components were stirred for one hour by means of a beads mill to obtain liquid H.

| [Liquid I] | |
|---|---|
| Bengara 211 | 1.0 part by weight |
| Yuka Former AM75 202 | 7.5 parts by weight |
| KF-56 | 0.25 part by weight |
| Ethanol | 39.25 parts by weight |

The above components were stirred for one hour by means of a beads mill to obtain liquid I.

| | |
|---|---|
| [Liquid H] | 52.0 parts by weight |
| [Liquid I] | 48.0 parts by weight |

The above liquids were stirred by means of a magnetic stirrer to obtain hairdye E.

Comparative Example 6

| | |
|---|---|
| Red No. 227 aluminum lake (manufactured by Kishi Kasei Co., Ltd.) | 1.8 part by weight |
| Yellow No. 5 aluminum lake (manufactured by Kishi Kasei Co., Ltd.) | 2.3 parts by weight |
| Konjo 302 (Prussian blue; trade name of Daito Kasei Co., Ltd.) | 1.4 part by weight |
| Titanium, oxide CR 50 (trade name of Ishiwara Sangyo Co., Ltd.) | 0.5 part by weight |
| Yuka Former AM75 202 | 15.0 parts by weight |
| KF-56 | 0.5 part by weight |
| Ethanol | 78.5 parts by weight |

The above components were stirred for one hour by means of a beads mill to obtain hairdye F.

The hairdyes 1 to 5 and the hairdyes A to F were used to carry out the following tests.

Test 1: redispersibility test (aging test for practical use)

An applicator shown in FIG. 1 was charged with the hairdyes 1 to 5 and the hairdyes A to F and left for standing upward for one month. Then, it was vibrated up and down at a stroke of about 20 cm and a rate of about 1 Hz for about one minute, and lines were drawn on a glass plate with the above applicator (brush) to compare a hue and a density of the drawn lines with those of the initial ones. The difference between them was observed by naked eyes.

o: little change
Δ: a little change in hue or density
x: extremely faint or impossible to draw Test 2: feeling check The hairdyes 1 to 5 and the hairdyes A to F after finishing the test 1 were used to apply them on hairs of 20 monitors to check the feeling.

o: natural hue and tensible; supple and natural finishing
Δ: unnatural hue and a little stiff feeling
x: hue is separated into two or more colors; hair is so stiff as to become a bar form The results of the tests 1 and 2 are summarized in Table 1.

TABLE 1

| | Test results | |
|---|---|---|
| | Test 1 | Test 2 |
| Example 1 | o | o |
| Example 2 | o | o |
| Example 3 | o | Δ |
| Example 4 | o | Δ |
| Example 5 | o | o |
| Comparative Example 1 | x | x |
| Comparative Example 2 | x | x |
| Comparative Example 3 | x | x |
| Comparative Example 4 | o | x |
| Comparative Example 5 | x | x |
| Comparative Example 6 | Δ | x |

Since the hairdyes giving the bad results in the test 1 are inferior in a coloring power, they are applied in large amounts, which increases a stiff feeling and provides the bad results as well in the test 2.

What is claimed is:

1. A temporary hairdye comprising 0.1 to 20% of an N-methacryloylethyl-N,N-dimethylammonium.α-N-methylcarboxybetain.butyl methacrylate copolymer as a dispersant, 1 to 10% of coloring components comprising titanium black and at least one pigment selected from the group consisting of iron oxide red, yellow iron oxide and black iron oxide, and 70 to 98.9% of an alcoholic solvent having 4 or less carbon atoms.

2. A temporary hairdye as described in claim 1, containing ethanol as said alcoholic solvent.

3. A temporary hairdye as described in claim 1, containing ethanol as said alcoholic solvent and 0.3 to 10% of the N-methacryloylethyl-N,N-dimethylammonium.α-N-methylcarboxybetain.butyl methacrylate copolymer.

4. A temporary hairdye as described in claim 1, containing ethanol as said alcoholic solvent and 2 to 8% of the N-methacryloylethyl-N,N-dimethylammonium.α-N-methylcarboxybetain.butyl methacrylate copolymer.

5. A process for producing a temporary hairdye as described in claim 1, comprising preparing a first solution by dissolving an N-methacryloylethyl-N,N-dimethylammonium.α-N-methylcarboxybetain.butyl methacrylate copolymer as a dispersant in ethanol and then adding and dispersing titanium black therein;

preparing a second solution by mixing ethanol and said copolymer and dispersing therein titanium black and at least one pigment selected from the group consisting of iron oxide red, yellow iron oxide and black iron oxide; and mixing said first solution and said second solution.

6. A process for producing a temporary hairdye as described in claim 5, wherein said titanium black is present in said second solution in an amount greater than 10 weight percent relative to said pigment in said second solution.

* * * * *